US012100505B2

(12) United States Patent
Schmoll

(10) Patent No.: US 12,100,505 B2
(45) Date of Patent: Sep. 24, 2024

(54) MEDICAL PATIENT VALIDATION DEVICE

(71) Applicant: B. Braun Melsungen AG, Melsungen (DE)

(72) Inventor: Horst Schmoll, Guxhagen (DE)

(73) Assignee: B. Braun Melsungen AG, Melsungen (DE)

( * ) Notice: Subject to any disclaimer, the term of this patent is extended or adjusted under 35 U.S.C. 154(b) by 260 days.

(21) Appl. No.: 17/642,282

(22) PCT Filed: Sep. 17, 2020

(86) PCT No.: PCT/EP2020/076003
§ 371 (c)(1),
(2) Date: Mar. 11, 2022

(87) PCT Pub. No.: WO2021/053082
PCT Pub. Date: Mar. 25, 2021

(65) Prior Publication Data
US 2022/0301702 A1    Sep. 22, 2022

(30) Foreign Application Priority Data
Sep. 17, 2019   (DE) ............... 10 2019 124 995.3

(51) Int. Cl.
 *G16H 40/40*   (2018.01)
(52) U.S. Cl.
 CPC ................... *G16H 40/40* (2018.01)
(58) Field of Classification Search
 None
 See application file for complete search history.

(56) References Cited

U.S. PATENT DOCUMENTS

| 6,985,870 B2 | 1/2006 | Martucci et al. |
| 2005/0102167 A1* | 5/2005 | Kapoor ............ G16H 40/20 705/3 |

(Continued)

FOREIGN PATENT DOCUMENTS

DE    102016005131 A1    11/2017

OTHER PUBLICATIONS

Hamadaqa et al. ("Highly Secured Implantable Medical Devices," 2018 International Conference on Innovations in Information Technology (IIT), AI Ain, United Arab Emirates, 2018, pp. 7-12) (Year: 2018).*

(Continued)

*Primary Examiner* — Christopher B Tokarczyk
(74) *Attorney, Agent, or Firm* — Christopher A. Rothe; CM Law

(57) ABSTRACT

A validation system includes at least one medical device for connection to a patient. Both the medical device and the patient have at least one identification marker. The validation system also has an identification device with a display that is configured to read the identification markers. The validation system further includes a server that communicates with the at least one medical device and the identification device. The server assigns the at least one medical device to a corresponding patient according to an assignment process. A reviewer reviews the assignment in a reviewing process that is independent of the assignment process. A method ensures that at least one item of patient information and/or location information is assigned to at least one medical device and that the assignment is reviewed.

8 Claims, 1 Drawing Sheet

(56) References Cited

U.S. PATENT DOCUMENTS

| | | | |
|---|---|---|---|
| 2014/0379369 A1* | 12/2014 | Kokovidis | ............. G16H 40/67 |
| | | | 705/2 |
| 2016/0051751 A1 | 2/2016 | Silkaitis et al. | |
| 2017/0147918 A1* | 5/2017 | Karani | ............. G06K 19/07775 |
| 2018/0253682 A1* | 9/2018 | Gilman | ................ G06Q 10/087 |

OTHER PUBLICATIONS

Written Opinion received in International Application No. PCT/EP2020/076003 dated Nov. 20, 2020, with translation, 13 pages.
Search Report received in German Application No. 10 2019 124 995.3 dated Apr. 30, 2020, with translation, 13 pages.
Search Report received in International Application No. PCT/EP2020/076003 dated Nov. 20, 2020, with translation, 5 pages.

* cited by examiner

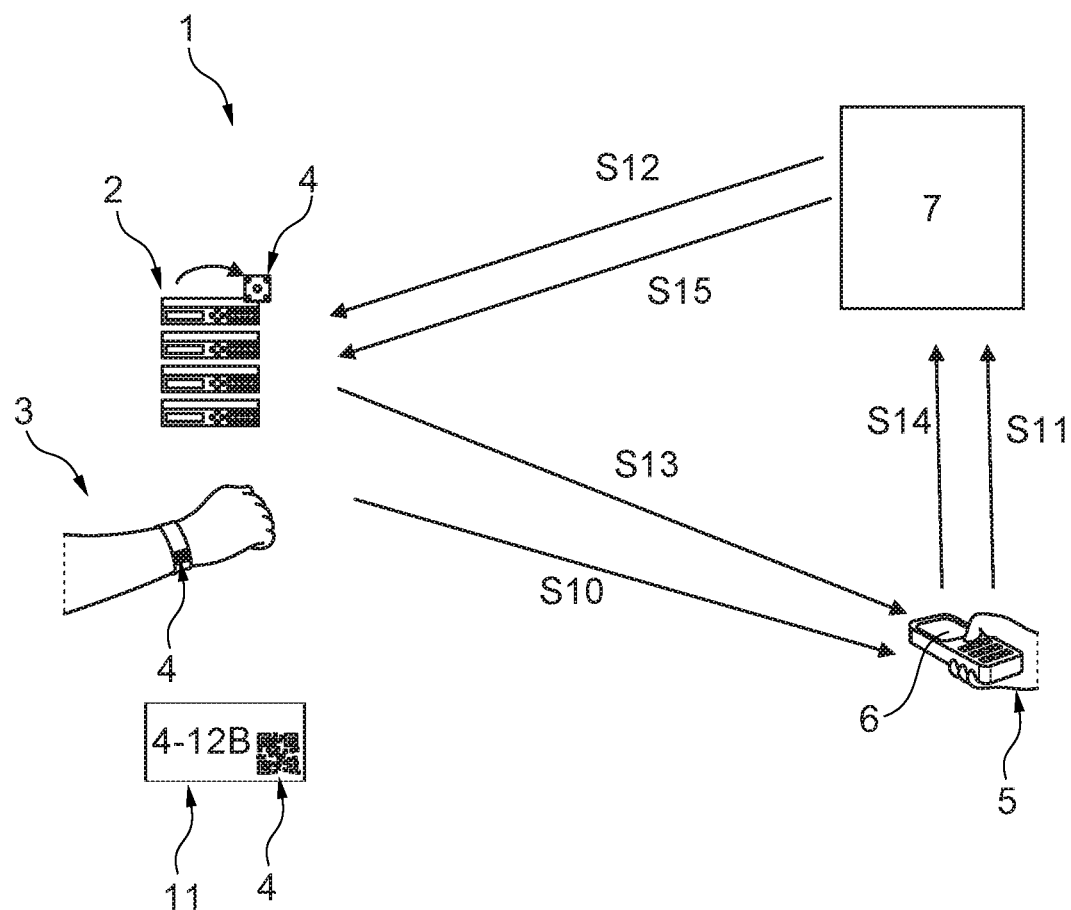

MEDICAL PATIENT VALIDATION DEVICE

CROSS-REFERENCES TO RELATED APPLICATIONS

This application is the United States national stage of International Application No. PCT/EP2020/076003, filed Sep. 17, 2020, and claims priority to German Application No. 10 2019 124 995.3, filed Sep. 17, 2019. The contents of International Application No. PCT/EP2020/076003 and German Application No. 10 2019 124 995.3 are incorporated by reference herein in their entireties.

FIELD

The present disclosure relates to a validation system (device) and a checking method for ensuring that at least one piece of patient information and/or location information is securely assigned to a medical device and that the assignment is checked.

BACKGROUND

In clinical practice, medical devices are connected to patients. Both the medical device and the patient are identified by means of a 'reader' and the data packet read out in the process is sent to a server. The read out data contains in particular patient information and/or location information, which is assigned to at least one medical device. The location information is preferably information about the location of the patient's bed or the patient's room as well as the medical devices, which are mostly located in the patient's room or respectively in the vicinity of the patient's bed.

Data transfer is provided between the server and at least one medical device, such as one or more infusion pumps. Here, the medical device may receive, for example, a prescription and/or medication for a particular patient. In this data transfer, it is important that the data to be received by the medical device reach the correct patient.

Methods for the logical assignment of medical products to patients are already known. These are used, for example, for the automatic programming of infusion pumps. Current implementations in which medical products are logically assigned to a patient are not simply error-proof with regard to the IEC 60601-1 standard. In clinical practice, this means that the assignment information is not fully trustworthy and requires additional validation by the user. For example, therapy orders sent to an infusion pump have to be validated and confirmed by the user before the infusion is started.

According to the current prior art, the server knows which patient ID belongs to a particular medical product. While the server is able to forward information for this patient ID to the medical product, the process is not fail-safe. An error, as can occur in previous systems, cannot be detected according to this prior art and may lead to misrouting.

In other words, current implementations allow medical products to be logically assigned to patients only. However, validation or verification of this assignment is not provided. It is furthermore disadvantageous that locations such as a room or an ID of the patient's bed are not covered.

SUMMARY

The present invention is therefore based on the object of developing a validation system for the assignment of at least one medical device to a patient, which avoids or at least reduces the disadvantages of the prior art.

The core of the present invention is to provide a validation system comprising at least one medical device, an identification device, and a server that communicates with the at least one medical device and the identification device and which is provided and configured to assign the at least one medical device to a corresponding patient and/or a patient's bed or respectively patient information and/or location information according to an assignment process. The at least one medical device is connected or respectively connectable to a patient and both the medical device and the patient are provided or respectively providable with at least one identification marker. The identification device is provided with a display and is designed and configured to read out the identification markers.

According to the invention, a reviewing means is additionally arranged, which is provided and configured to review the assignment of the at least one medical device to the corresponding patient and/or patient's bed or respectively the corresponding patient information and/or location information in a reviewing process independent of/separate from the assignment process via a first transaction ID generated by the server.

In other words, this means that the patient and/or the patient's bed and the at least one medical device are each provided with an identification marker, which is read out according to an assignment process via the identification device. The read data from the identification marker of the patient and/or the patient's bed and the at least one corresponding medical device are sent as a data packet to the server. In a reviewing process, a first transaction ID is subsequently generated based on the data packet received from the server. The generated first transaction ID enables reviewing the assignment of the at least one medical device to the corresponding patient and/or patient's bed or respectively patient information and/or location.

The validation system described above provides the basis for medical server applications that use data from multiple medical devices/medical products linked/connected to a single patient and/or location.

Since it is furthermore preferred if the identification device is designed as a connection device, the validation system enables a connection between the server or the server address and the medical device and/or patient and/or the patient's bed and/or connected systems in order to securely assign data, transmitted from the medical device to the server, to the patient and/or to the patient's bed. This enables a user, in particular a physician, to make a diagnosis and/or to adjust treatment. In particular, it is preferred if moreover the connection between the server or the server address and the medical device and/or the patient and/or the patient's bed is established and used via a remote control. It is preferred if the identification device reads the identification markers optically, for example via infrared. This offers the advantage that the user/operator of the identification device can/may have a variable distance and/or angle to the identification marker.

This makes it possible to dynamically ensure a secure, logical assignment and linking of medical products to patient information and/or location information. It is provided that the patient information and/or location information is contained in technical or medical data reported by the at least one medical device/medical product and enables the linking/assignment of data of a plurality of medical devices/medical products with/to a patient and/or to a location. Any data received from a medical-product side, such as a therapy prescription for a particular patient, can thus be safely reviewed to ensure that it is being sent to the exact medical device that is connected to the correct patient and/or location.

It is preferred if the identification marker is configured as a QR code or barcode or an identification number and comprises at least a device ID, a patient ID, and/or a location ID. In other words, this means that the patient wears, for example, a wristband with a corresponding identification marker that has the patient ID. Furthermore, it is alternatively or additionally provided that the patient's bed comprises an identification marker that outputs the location ID, preferably the ID of the patient's bed and/or the associated room. An identification marker is also attached to the at least one medical device, which outputs the device ID. This has the advantage that the identification marker can be easily read out via the identification device. The identification device is preferably designed as a QR code reader and/or barcode reader or alternatively as an optical camera system.

It is preferred that the first transaction ID generated by the server is composed of the device ID, the patient ID, and/or the location ID. The healthcare organization maintains a list of unique identification elements for medical products, medical devices, patients, and/or locations. This is, for example, a patient wristband with a unique identification number or a QR code with information for identifying the medical products/medical devices or location information.

It is preferred if the medical device in the reviewing process is provided and configured to receive the first transaction ID and to send a modified second transaction ID to the server if the first transaction ID comprises the device ID. In other words, this means that the server sends the generated first transaction ID to the at least one medical device. The at least one medical device matches whether the first transaction ID includes the device ID corresponding to the at least one medical device. If this is the case, the at least one medical device displays a changed/modified second transaction ID on the screen of the identification device.

It is preferred if the server in the reviewing process is provided and configured to compare the received second transaction ID with the generated first transaction ID stored in the server. In other words, this means that the second transaction ID is sent from the identification device back to the server. The server compares the second transaction ID with first transaction ID, wherein the first transaction ID is/was stored in the server.

It is preferred if, in the event of a positive comparison in the medical device, the identification device in the reviewing process is provided and configured to visualize the positive assignment of the medical device to the patient and/or to the location in a preferably optical symbol on the display. This means that if the first transaction ID matches the second transaction ID, the assignment of the at least one medical device to the patient and/or location is treated as valid. The valid connection/assignment of the at least one medical device/product to the patient and/or the patient's bed or respectively to the patient information and/or location information is finally visualized by an optical symbol assigned to the identification device.

It is preferred if the server in the reviewing process is provided and configured to change the second transaction ID to a third transaction ID and to send it to the medical device. In other words, the second transaction ID received by the server is modified again and sent to the at least one medical device.

It is preferred if the medical device in the reviewing process is provided and configured to compare the received third transaction ID with the stored second transaction ID. The at least one medical device compares this modified third transaction ID with the second transaction ID stored in the at least one medical device.

It is preferred if, in the event of a positive comparison, the identification device in the reviewing process is provided and configured to visualize the positive assignment of the at least one medical device to the patient and/or to the location in a preferably optical symbol on the display. This means that if the second transaction ID matches the third transaction ID, the assignment of the at least one medical device to the patient and/or the patient's bed or respectively to the patient information and/or location information is treated as valid. The valid connection/assignment of the at least one medical device/product to the patient and/or location is finally visualized by an optical symbol on the screen of the identification device.

It is preferred if the validation system is provided and configured to group the patient information and/or location information from a plurality of medical devices/medical products associated with a single patient or location. In other words, this means that at this point in time, all data sent by the at least one medical device contains/comprises patient information and/or location information that allows combining data from a plurality of medical devices/medical products. In addition, the at least one medical device is configured for/capable of performing independent validations of incoming control orders.

In summary, the validation system makes it possible to review the assignment made in the assignment process. Thus, by means of the reviewing means, this review provides a channel for protecting against individual errors that is independent of the assignment process. Thus, the validation system offers the advantage of error-proof assignment of data from medical products/medical devices to a patient ID and/or a location ID and, through the reviewing process, enables data to be used in server applications for therapeutic decisions, to group data from a large number of medical products/medical devices belonging to a single patient/location, and to accept control data for remote control of medical products/medical devices.

Furthermore, the present invention relates to a controlling/checking/monitoring method for ensuring that at least one piece of patient information and/or location information is assigned to at least one medical device and that the assignment is reviewed, comprising the following steps.

In a first step, an identification marker is read out and a device ID, patient ID, and/or location ID is output as a data packet by an identification device. In a second step, this read-out data is sent as a data packet to a server. The server generates a first transaction ID from the device ID, patient ID, and/or location ID and sends the generated first transaction ID to the at least one medical device. In a further step, the first transaction ID is changed/modified to a second transaction ID if the first transaction ID has the device ID. This means that the at least one medical device checks whether its device ID is included in the first transaction ID. If this is the case, the first transaction ID is modified and shown on the display of the identification device.

In a subsequent step, the second transaction ID is sent back to the server and the second transaction ID received at the server is compared with the first transaction ID stored in the server. If the comparison matches, an optical symbol is visualized on the display of the identification device and the second transaction ID is changed to a third transaction ID in the server.

The third transaction ID is sent to the at least one medical device and the received third transaction ID is compared with the stored second transaction ID. In a final step, an optical symbol is visualized and displayed on the screen of the identification device if the comparison matches.

After successfully performing the above steps, the logical link/assignment of medical product/medical device to a patient and/or location is validated on both the server side and medical-device side.

By repeating this method, a plurality of multiple/different medical devices/medical products, such as multiple infusion pumps, dialysis machines, ventilators, physiological sensors, and/or the like, can be associated with or assigned to a single patient and/or location.

The present invention is provided for data transfer between medical devices and applications, for example two medical devices, pump 1 and pump 2, which communicate with each other via a server. During certain short interruptions/pauses in the method, the system continues to run and during long interruptions/pauses, the assignment process is initiated again.

BRIEF DESCRIPTION OF THE DRAWING FIGURE

The FIGURE is a schematic representation illustrating a validation system and a checking method according to the embodiment of the present disclosure.

DETAILED DESCRIPTION

A preferred embodiment of the present disclosure is described below based on the accompanying FIGURE. The FIGURE is merely schematic in nature and is provided for the purpose of understanding the invention. Identical elements are designated by the same reference signs.

The FIGURE is a representation illustrating a validation system 1 according to the embodiment of the present disclosure. The arrows labeled S10 to S15 shown in the FIGURE represent communication links/data paths, which are referred to as steps S10 to S15 in the following description. The validation system 1 according to the FIGURE has, among other things, a medical device 2. The medical device 2 is exemplified in the FIGURE by a plurality of infusion pumps. The medical device 2 and a depicted patient (patient arm) 3 or respectively a depicted patient's bed 11 each have an identification marker 4 as a further part of the validation system 1, formed as a QR code. The medical device 2 is connected to the patient 3 during operation (not shown) or is located in the vicinity of the patient's bed.

Furthermore, the validation system 1 has an identification device 5. The identification device 5 is configured to read the identification markers 4 from the medical device 2 and the patient 3 and/or the patient's bed 11. The identification device 5 reads out a device ID, a patient ID and/or a location ID/ID of the patient's bed from the identification markers 4. The identification device 5 has a display 6, which is configured to display/visualize information and/or symbols.

The FIGURE also shows a server 7 that communicates with both the medical device 2 and the identification device 5.

According to an assignment process, the identification device 5 reads out the identification markers 4 of the medical device 2 and of the patient 3 and/or of the patient's bed according to step S10. The read device ID, patient ID, and/or location ID are transmitted/sent to the server 7 as a data packet in a step S11.

The subsequent steps are performed according to a reviewing process. Here, in step S12, the server 7 generates a first transaction ID 8 from the received device ID, patient ID, and/or location ID and sends this first transaction ID 8 to the medical device 2. The medical device 2 checks whether the device ID corresponding to the medical device 2 is contained in the received first transaction ID 8.

If this is the case, the display of the medical device 2 shows a modified second transaction ID 9 according to step S13. The modification ensures that the transaction ID 8 was routed via the medical device 2. This modified second transaction ID 9 is read in by the identification device 5.

In step S14, the second transaction ID 9 is sent back to the server 7 and is compared with the first transaction ID 8 stored in the server 7. In case of a positive comparison of the second transaction ID 9 with the first transaction ID 8, the identification device 5 is adapted to visualize the positive assignment of the medical device 2 to the patient 3 and/or to the patient's bed 11 according to the location in an optical symbol on the display 6 and to designate the assignment as valid.

In a step S15, the server 7 modifies the second transaction ID 9 into a third transaction ID 10 and sends the third transaction ID 10 to the medical device 2. The medical device 2 compares the received third transaction ID 10 with the stored second transaction ID 9. In case of a positive comparison of the third transaction ID 10 with the second transaction ID 9, the identification device 5 is configured to visualize the positive assignment of the medical device 2 to the patient 3 and/or to the patient's bed 11 according to the location in a visual symbol on the screen/display of the medical device 2 and to designate the assignment as valid.

In addition, it is preferred if the positive assignment or validation is additionally shown on the display of the identification device 5 in a further step S16. This information about the positive validation is reported back to the user/operator via the identification device 5, for example, in an optical, acoustic, or haptic/vibrating manner.

After performing these foregoing steps S10 to S15 or S16, respectively, all data sent from the medical device/product 2 includes patient information and/or location information that allows a plurality of medical devices 2 to be combined, and the medical device 2 is further provided to perform independent validation of incoming checking orders.

In particular, it is provided that the assignment process can be performed independently of the reviewing process.

The invention claimed is:
1. A validation system comprising:
at least one medical device configured to be connected to a patient;
at least one identification marker associated with the at least one medical device and the patient;
an identification device comprising a display, the identification device configured to read out the at least one identification marker;
a server which communicates with the at least one medical device and the identification device, the server being configured to assign the at least one medical device to the patient according to an assignment process; and
a reviewing means configured to review an assignment of the at least one medical device to the patient in a reviewing process independent of the assignment process via a first transaction ID generated by the server, the first transaction ID comprising at least one of a device ID, a patient ID, and a location ID, and the at least one medical device being configured to receive the first transaction ID during the reviewing process and to send a modified second transaction ID to the server when the first transaction ID comprises the device ID, wherein the server in the reviewing process is provided and configured to compare the modified second transaction ID with the first transaction ID and validate a positive assignment of the at least one medical device to the patient and/or to the location upon determining that the modified second transaction ID matches the first transaction ID.

2. The validation system according to claim 1, wherein the at least one identification marker is configured as a QR code or an identification number and comprises at least one of a device ID, a patient ID, and a location ID.

3. The validation system according to claim 1, wherein the identification device in the reviewing process is configured to display the positive assignment of the at least one medical device to the patient and/or to the location when the modified second transaction ID matches the first transaction ID.

4. The validation system according to claim 1, wherein the validation system is configured to group patient information and/or location information from a plurality of medical devices/products associated with a single patient or location.

5. A validation system comprising:
at least one medical device configured to be connected to a patient;
at least one identification marker associated with the at least one medical device and the patient;
an identification device comprising a display, the identification device configured to read out the at least one identification marker;
a server which communicates with the at least one medical device and the identification device, the server being configured to assign the at least one medical device to the patient according to an assignment process; and
a reviewing means configured to review an assignment of the at least one medical device to the patient in a reviewing process independent of the assignment process via a first transaction ID generated by the server,
the first transaction ID comprising at least one of a device ID, a patient ID, and a location ID, and
the at least one medical device being configured to receive the first transaction ID during the reviewing process and to send a modified second transaction ID to the server when the first transaction ID comprises the device ID,
wherein the server is configured to change the modified second transaction ID to a third transaction ID and to send it to the medical device during the reviewing process.

6. The validation system according to claim 5, wherein the at least one medical device is configured to compare the third transaction ID with the modified second transaction ID during the reviewing process.

7. The validation system according to claim 6, wherein at least one of the identification device and the medical device is provided and configured to display a positive assignment of the at least one medical device to the patient and/or to the location when the third transaction ID matches the modified second transaction ID during the reviewing process.

8. A method for ensuring that at least one piece of patient information and/or location information is assigned to at least one medical device in an assignment and that the assignment is reviewed, the method comprising the steps of:
reading an identification marker and outputting at least one of a device ID, patient ID, and location ID as a data packet by an identification device;
sending the data packet to a server;
generating a first transaction ID from the at least one of a device ID, patient ID, and location ID, and sending the first transaction ID to the at least one medical device;
changing the first transaction ID to a second transaction ID if the first transaction ID has the device ID;
displaying the second transaction ID on a display on the at least one medical device;
reading out the second transaction ID with the identification device;
sending the second transaction ID to the server;
comparing the second transaction ID with the first transaction ID;
changing the second transaction ID to a third transaction ID in the server and sending the third transaction ID to the at least one medical device;
comparing the third transaction ID with the second transaction ID; and
displaying an optical symbol on the display on the at least one medical device if the third transaction ID matches the second transaction ID.

* * * * *